United States Patent [19]
Smith

[11] 4,079,545
[45] Mar. 21, 1978

[54] TREATMENT OF SEEDS WITH C3 HALOHYDROCARBONS

[75] Inventor: W. Ray Smith, Germantown, Tenn.

[73] Assignee: Smith & Pinckard, Inc., Germantown, Tenn.

[21] Appl. No.: 583,388

[22] Filed: Jun. 3, 1975

[51] Int. Cl.$^2$ .................. A01C 1/06; A01N 21/02; A01N 9/36; A01N 9/12
[52] U.S. Cl. .................. 47/57.6; 71/77; 71/126; 424/167; 424/200; 424/202; 424/211; 424/216; 424/244; 424/286; 424/289; 424/349; 424/350; 424/351
[58] Field of Search .......... 71/77, 126; 47/57.6; 424/350, 351

[56] References Cited

U.S. PATENT DOCUMENTS

| | | | |
|---|---|---|---|
| 2,435,204 | 2/1948 | Davidson | 71/126 |
| 2,759,010 | 8/1956 | Lorenz et al. | 424/216 X |
| 2,895,872 | 7/1959 | Meuli | 71/77 X |
| 2,921,410 | 1/1960 | Merritt | 71/77 |
| 3,005,752 | 10/1961 | McBeth et al. | 424/350 |
| 3,036,951 | 5/1962 | Disselnkotter et al. | 424/351 X |
| 3,063,825 | 11/1962 | Weil | 71/126 X |
| 3,093,472 | 6/1963 | Homeyer et al. | 71/126 |
| 3,195,997 | 7/1965 | Arai et al. | 71/126 X |
| 3,255,076 | 6/1966 | Weil et al. | 424/351 |
| 3,258,394 | 6/1966 | Hall et al. | 260/943 X |
| 3,617,247 | 11/1971 | Chiles, Jr. | 71/77 |
| 3,728,099 | 4/1973 | Chiles, Jr. | 71/77 |
| 3,765,865 | 10/1973 | Smith et al. | 71/113 |

OTHER PUBLICATIONS

Cotton Disease Council Proceedings (1961), p. 40.
Cotton Disease Council Proceedings (1962), pp. 45, 46, 49, 50.
Phytopathology, 52, (1962), Pinckard et al., p. 747.
Phytopathology, 54, (1964), Birchfield et al., pp. 393-394.
Smith et al., Weed Science, 19, (1971), pp. 346-349.

Primary Examiner—Joseph Paul Brust
Attorney, Agent, or Firm—Jones, Tullar & Cooper

[57] ABSTRACT

This invention relates to the use of C$_3$ halogenated hydrocarbons alone or in combination with other agronomic adjuvants such as nemiticides, insecticides, fungicides and herbicides for treating agronomic seeds, and mixtures of agronomic seeds with weed seeds to retard weed growth and/or stimulate growth of the agronomic seeds. The method of the invention is particularly useful for treating mixtures of cotton seeds and cocklebur seeds to reduce cocklebur seed germination.

15 Claims, No Drawings

TREATMENT OF SEEDS WITH C3 HALOHYDROCARBONS

BACKGROUND OF THE INVENTION

This invention relates to a method for increasing the germination and growth of useful agricultural crop seeds, and to the prevention or retardation of the germination of weed seeds in admixture with the useful agricultural crop seeds. In particular, this invention is directed to the treatment of agronomic seeds particularly cotton seeds and to mixtures of cotton seeds with cocklebur seeds, whereby such seeds are provided with a coating of a $C_3$ saturated or ethylinically unsaturated halogenated hydrocarbons, especially mixtures of chlorinated propanes and propenes. The invention also relates to coating seeds with known agronomic adjuvants in conjunction with the aforementioned halogenated hydrocarbons. Particularly preferred adjuvants are mixtures of phosphate esters such as 0,0-diethyl-S-2(ethylthio)ethyl phosphorodithioate and carbamylalkenyl phosphorous containing esters such as the dimethyl phosphate of 3-hydroxy-N-methyl-cis-crotonamide.

In the past seeds have been treated with various materials to protect the seeds prior to germination; such treatments generally have had adverse effects on the subsequent germination of the seeds.

U.S. Pat. Nos. 3,617,247 and 3,728,099 disclose the use of carbamylalkenyl phosphorous esters, alone or in combination with various materials including 0,0-diethyl-S-2(ethylthio)ethyl phosphorodithioate.

The use of 1-chloro-1,2-dibromoethane to accelerate germination and growth of plants is described in U.S. Pat. No. 3,195,997. That same patent teaches that $C_3$ halogenated hydrocarbons have an adverse effect on plant growth when contacted with seeds.

Halogenated hydrocarbons such as Nemagon and Fumizone have been shown to be fungicidal by Dr. J. A. Pinckard who combined a dust formulation and applied it to cottonseed as a seed hopper box fungicide. (Proceedings of the Cotton Disease Council 1961–1962). Three pounds per acre of a 50% Nemagon dust containing Terraclor and 4.6% dieldrin increased stands of cotton seedlings 46% (average of 20 tests in four states).

Reduction of nematode (Reinform sp.) infection in cotton roots was shown by Wray Birchfield and J. A. Pinckard by means of the above formulation in 1961. (Phytopathology 52:747, 1962). Other plant disease causing agents such as members of the genus Pythium have been reduced by means of soil applications of the halogenated propanes and propenes such as Namagon, Fumizone, D-D and Telone. McBeth reported control of Pythium species with Nemagon (2–3 lbs. per acre) when used as a seed treatment or as a planter box application. (Proceedings, Cotton Disease Council, 1962. Published by the National Cotton Council.)

The common cocklebur (members of the genus Xanthium) is a pest weed in cotton fields and its seed passes through the cotton gins along with cottonseed, contaminating plating seed stocks. Reducing the number of cockelbur seeds tolerated by the seed purity standards allowable by state seed laws has made it desirable to remove such seeds either by mechanical or chemical means or by interfering with the germination of these pest weeds without harm to cottonseed planting stocks. It has been shown that the use of certain chemicals such as alkyl acetates and alcoholic acetic acid would reduce or interfere with the germination of cocklebur seed, see U.S. Pat. No. 3,765,865 and Weed Science 19 346-349 (1970). This method, however, has certain drawbacks with mechanically delinted cottonseed and "zip-flame" delinted cottonseed including the cost of drying the seed after treatment with the acetic acid formulation.

Mechanical removal of cocklebur seed from mechanically delinted cottonseed is not practical. Mechanical removal of cocklebur seed from acid delinted cotton seed can be accomplished.

DESCRIPTION OF THE INVENTION

As stated above, this invention relates to a method for increasing the germination and growth of useful agricultural crop seeds, and to the prevention or retardation of the germination of weed seeds in admixture with useful agricultural crop seeds. In another aspect this invention relates to seeds or seed mixtures treated in accordance with the invention. In particular, this invention is directed to the treatment of agronomic seeds, particularly cotton seeds, and to mixtures of cotton seeds with cocklebur seeds (members of the genus Xanthium, e.g. Xanthium pensylvanicum Wallr.) whereby such seeds are provided with a coating of a $C_3$ saturated or ethylinically unsaturated halogenated hydrocarbons, especially mixtures of chlorinated or chlorobrominated propanes and propenes. The invention also relates to coating seeds with mixtures of the aforementioned halogenated hydrocarbons with phosphate esters such as 0,0-diethyl-S-2(ethylthio)ethyl phosphorodithioate and/or carbamylalkenyl phosphorous containing esters such as the dimethylphosphate of 3-hydroxy-N-methyl-cis-crotonamide.

It has further been discovered that the $C_3$ halohydrocarbons in addition to enhancing germination and growth of cotton seeds and/or reduce germination and growth of cockelbur seeds, also functions as an active solvent for certain pesticides such as the phosphate esters and/or carbamylalkenyl phosphorous containing esters, described herein, forming solutions with relatively low clouding or precipitation points which prevent "freeze-out" of these pesticidal mixtures during storage. Freeze out being indicated by a separation of solid material which requires significant effort to redissolve.

The halogenated $C_3$ hydrocarbons which are used in carrying out this invention are halogenated $C_3$ hydrocarbons where the halogen is chlorine, bromine, or mixtures thereof. The $C_3$ hydrocarbon may be saturated or unsaturated, or thereof. Particularly useful compounds include 1,3-dichloropropene; 3,3-dichloropropene; 1,2-dichloropropane, 2,3-dichloropropene and 1,2-dibromo-3-chloropronane or mixtures thereof. Preferably the $C_3$ halogenated hydrocarbon contains 2 to 4 halogen atoms.

A particularly useful material is the material sold as D-D soil fumigant, a liquid, consisting to $C_3$ hydrocarbons including 1,3-dichloropropene; 3,3-dichloropropene; 1,2-dichloropropane; 2,3-dichloropropene and related $C_3$ chlorinated hydrocarbons, having a density (lb./gal. at 68° F.) of 9.9, an approximate boiling range of 194° to 320° F., a minimum chlorine content of 55 weight percent and a minimum content of 1,3-dichloroprene-1 of 50 weight percent.

Another particularly useful material is sold as Nemagon C soil fumigant consisting of not less than 95 weight percent 1,2-dibromo-3-chloropropene and not more than 5% of other nematocidally active, halogenated $C_3$ compounds, having a boiling point of 385° F. at 760 mm Hg and a crystallization temperature range of 35° to 41° F.

Yet another particularly useful material is sold as Telone comprising 84% 1,2-dibromo-3-chloropropane and 3% related $C_3$ hydrocarbons.

The halogenated hydrocarbons may be utilized in conjunction with various agronomic adjuvants including insecticidal growth stimulants such as the composition comprising carbamylalkenyl phosphorous-containing esters characterized by the formula:

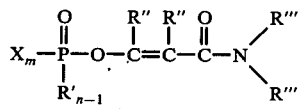

wherein X is a member of the class of radicals consisting of RO—, RNH— and $R_2N$— in which R is alkyl group containing up to 6 carbon atoms, R' is a monovalent hydrocarbon radical; each R'' is a member of the class consisting of a hydrogen atom and an alkyl radical; each R''', taken singly, is a member of the class consisting of a hydrogen atom, a monovalent hydrocarbon radical, an alkoxyaryl radical, a cyanoaryl radical, and taken together in combination, a divalent hydrocarbon radical with 4 to 5 saturated carbon atoms in a chain between the two valences; $m$ is an integer of 1 to 2; and $n = 3 - m$. Thus, for example, R is any alkyl radical of up to 6 carbon atoms such as methyl, ethyl, isopropyl, butyl, etc. R' is any monovalent hydrocarbon radical such as methyl, ethyl, isobutyl, 3-hexyl, decyl, octadecyl, oleyl, propargyl, etc. R'' is the same or difference and is a hydrocarbon atom of a methyl, ethyl, or isobutyl group. Taken singly, each R'' is the same and is a hydrogen atom or any monovalent hydrocarbon radical such as was exemplified for R'. Taken together, the R''s are a divalent hydrocarbon radical with 4 to 5 saturated carbon atom in a chain between the two valences such as a tetramethylene radical, as in a pyrrolidyl group, or a pentamethylene radical, as in a piperidyl group, and homologues thereof. It will be noted from the above formula that when the $m$ is the integer of 1, $n -1+1$ and the compound is a phosphate; and that when $m$ is the integer 2, $n-1=0$ and the compound is a related phosphate. Preferably, the compounds have alkyl groups as the hydrocarbon radicals, and it is further preferred that the compounds be derivatives of N,N-dialkyl alpha-chloroacetoacetamide.

Insecticidal compositions having the abovedescribed essential ingredient are more particularly disclosed in U.S. Pat. No. 2,802,855 to Richard R. Whetstone and Allen R. Stiles and U.S. Pat. No. 3,258,394 to Walter E. Hall and Donald D. Phillips.

In conjunction with the above compounds or in place of them there can be utilized after agronomic adjuvants, for example, insecticidal or fungicidal materials, such as the compound having the chemical name, O,-diethyl-S-(ethylthio)ethyl phosphorodithioate and referred to by the trade name "Di-Syston", which is an insecticide, miticide, and/or fungicide as will appear from Lorenze et al U.S. Pat. No. 2,759,010, and Farbenfabriken Bayer French Pat. No. 1,421,510, patented Nov. 8, 1965, to which Hans Scheinplug et al U.S. Pat. No. 3,459,857, corresponds. The remaining thiol- or thionothiol-phosphoric (-phosphonic) acid esters disclosed in the foregoing patents which generically embrace the compound referred to as "Di-Syston" may be also used alone or in conjunction with the carbamylalkenyl phosphourous-containing esters. The thiol- or thionothiol-phosphoric (-phosphonic) acid esters can be represented by the general formula:

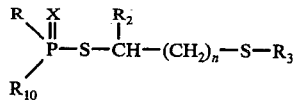

in which R is selected from the group consisting of alkyl, alkoxy, cycloalkoxy, and aryl radicals, $R_1$ is an alkyl radical, $R_2$ is selected from the group consisting of hydrogen and lower carboalkoxy radicals, $R_3$ is an alkyl radical, X is selected from the group consisting of oxygen and sulfur, and $n$ is a whole number having a value from 0 to 1.

Of course, most of the other known fungicide materials which are used to treat seeds in the normal fungicidal manner may be used in conjunction with the halogenated $C_3$ hydrocarbon alone, or in admixture with the carbamylalkenyl phosphorous-containing esters to produce excellent growth enhancing in the resulting seedlings and plants of the treated seeds. Broadly speaking, most any fungicide which is referred to as systemic or contact fungicide may be used in the combination in accordance with the practice of this invention. By systemic fungicidal composition it is meant to include those fungicides which penetrate into the seed or seedling and are disseminated (trans-located) therein without inquiry to the plant, but still act effectively as fungicides. Examples of systemic fungicides which may be used in the combination besides the thio-phospho acid esters, such as the compound O,O-diethyl-S-(ethylthio)ethyl phosphorodithioate ("Di-Syston") include the compounds known by the chemical names: 1,4-dichloro-2,5-dimethoxybenzene, also known by the trademark, "Demosan 65-W" and 2,3-dihydro5-carboxanilido-6-methyl-1,4-oxathin, also known by the trademark, "Vitavax" and the common name "Carboxan". Typical contact fungicides which may be used are the compounds of the chemical names: zinc, manganese and sodium salts of ethylenebisthiocarbamate; bis-(dimethylithiocarbamyl) disulfide; zinc polyethylenethiuram disulfide complex, also known by the trademark, "Polyram"; zinc trichlorophenate; the chemical formulation known by the trademark, "Terracoat L-21" which contains 22.7% pentachloronitrobenzene (PCNB) and 11% 5-ethoxy-3-trichloromethyl-1,2,4-triodizole, the latter known by the trademark, "Terrazole", all of which are admixed in a hydrocarbon solvent; and the chemical formulation of 72% concentration of 2-(thiocyano methylthio)benzothiazole, known by the trademark, "Busan 72".

The foregoing fungicidal materials may be used either alone, with the carbamylalkenyl phosphorous-containing esters or in conjunction with other fungicides. As it is well known in the seed treating art, commercially available cottonseeds are pretreated with a fungicide-disinfectant, i.e., Thiram, Captan (43% N-[(trichloromethyl) thio]-4-cyclohexane-1,2-dicarboxide and 43% bis(dimethyl thio-carbamoyl) disulfide and others or "Ceresana". Thus, it is to be understood that the invention is meant to include these materials by implication as well as the use of the other known fungicides. For example, the foregoing fungicidal materials referred to by the trademarks, "Demosan 65W" and "Captan" may be used together with the carbamylalkenyl phosphorous-containing esters in treating the seeds to produce excellent growthenhancing results. Other combinations which have been found in achieving growth-enhancing of the seedlings and high harvestable yields of the crop from the treated seeds include admixing the preferred carbamylalkenyl phosphorous containing ester, i.e., the dimethyl phosphate of 3-hydroxy-N-methyl-cis-crotonamide, dissolved in acetone known by the trademark "Azodrin", with one of the fungicide disinfectants (such as the composition known as phenyl mercury, plus "Demosan 65W, "Terracoat L-21", and/or the mixture comprising "Captan", "Vitzvax 735D" with "Azodrin". Particularly advantageous growth-enhancing and high harvestable yields are obtained by coating the seeds with a composition comprising the halocarbon, "Azodrin", and either one of the systemic fungicides, "Vitavax 735D" or "Demosan 65W". This combination, produces better fungicidal protection of the seeds and seedlings as compared to seeds which are only treated with either of the fungicides alone. The reason for the enhanced fungicidal protection is that the insecticide, "Azodrin", i.e., the dimethyl phosphate of 3-hydroxyl-N-methyl-cis-crotonamide in acetone, assists the fungicide to act as a systemic. This phenomenon occurs because of the solvent action of "Azodrin" on the fungicide which in turn permits both the active ingredients, i.e., the insecticide and the fungicide to penetrate the seed coat. (Go-Better or Azodrin also acts as a seed disinfectant).

The amount of the $C_3$ halohydrocarbon utilized as a seed treating reagent, as well as additional adjuvants employed in conjunction with the $C_3$ halohydrocarbon, is dependent upon many factors, including the particular compound used, the kind and quality of seed employed, the method and condition of application and the particular problem being controlled. Such considerations are, however, within the skill of the agronomic or horticultural art. In general, however, it is recommended that $C_3$ halohydrocarbon be applied to seeds in a weed seed controlling and/or useful seed growth enhancing amount, preferably in an amount of from about 0.2% to 0.5% by weight based on the total weight of the seed treated, although as little as about 0.1% or as much as 3% or even 4% or 5% of the halohydrocarbon may be employed with good results.

The composition comprising the $C_3$ halohydrocarbon utilized for treating seeds in accordance with the present invention may be applied to the seeds by any suitable coating means, such as spraying, brushing or dipping, for example, or may be otherwise applied as a solution, suspension or dispersion, as the sole active ingredient or in admixture or sequentially with additional active adjuvants. The seed treating compositions can be formulated using well known organic horticultural carriers, including hydrocarbons, acetone and non-phytotoxic oils of intermediate viscosity and volatility. It is also understood, of course, that seed treating compositions comprising solutions or suspensions, for example, in water, utilizing adjuvants such as fatty acid soaps, long chain fatty alcohols, alkyl aryl sulfonates, long chain alkyl sulfonates and the like. The solutions, suspensions or dispersions can likewise be applied by conventional application means such as set forth above. The compositions penetrate the surface of the seed so that the exterior of the seed is dry in appearance in a reasonable time.

Where the seed treating compositions contain the above described phosphate esters and/or carbamylalkenyl phosphorous containing esters, they are likewise employed in yield increasing amounts such as those described in U.S. Pat. Nos. 3,728,099 and 3,617,247, incorporated by reference.

The following illustrative examples of certain preferred embodiments of the invention will serve to more fully illustrate the full scope of the invention and it is understood that the invention is not limited thereby. All parts and percentages in the examples as throughout the specification are by weight unless otherwise specified.

EXAMPLE 1

Commercial cotton seed (TSPA 1633 variety) was test planted in the Rio Grande Valley in Texas in February, using the seed treatment mixtures per 100 pounds of seed stated in Table 1. The seed was treated with the mixture one day and planted the next.

The check was the TSPA 1633 seed washed free of pretreatment. Nemagon was employed at a 3/1 volume mixture with mineral spirits, the amount stated in Table 1 being Nemagon. The Go-Better or Azodrine was employed as a 56 weight percent solution in acetone, the amount stated in Table 1 being the solution.

Table 1

| Test No. | Nemagon (OZ) | Vitavax (OZ) | Go-Better or Azodrin (OZ) | Plant Emergence Counts - 3 Replicates | | |
|---|---|---|---|---|---|---|
| | | | | 1 | 2 | 3 |
| 1 | 0.69 | 0.69 | 1.84 | 27 | 21 | 9 |
| 2 | 1.38 | 1.33 | 3.69 | 20 | 16 | 17 |
| 3 | 3 | 3 | 8 | 24 | 22 | 21 |
| 4 | 6 | 6 | 16.0 | 32 | 32 | 23 |
| 5 | 12 | 12 | 32.0 | 25 | 30 | 29 |
| 6 | 6 | 3 | 8 | 22 | 24 | 24 |
| 7 | 12 | 3 | 8 | 20 | 27 | 19 |
| 8 | 24 | 3 | 8 | 17 | 14 | 10 |
| 9 | 48 | 3 | 8 | 3 | 1 | 0 |
| 10 | 48 | 3 | 0 | 5 | 8 | 0 |
| 11 | 48 | 0 | 0 | 4 | 7 | 2 |
| 12 | 0 | 0 | 8 | 8 | 24 | 19 |
| 13 | 6 | 3 | 4 | 12 | 19 | 8 |
| 14 | 6 | 3 | 16 | 4 | 5 | 2 |
| 15 | 0 | 3 | 8 | 12 | 17 | 15 |
| 16 | 0 | 3 | 0 | 19 | 22 | 19 |
| 17 | 0 | 3 | 8 | 21 | 24 | 18 |
| 18 | Check | — | — | 8 | 13 | 14 |

EXAMPLE 2

The following formulation, in addition to having the growth regulating properties showing herein, is a eutectic composition which prevents the freezeout of the Vitavax-Azodrin combination:

| | PBW |
|---|---|
| Nemagon C ($C_3$ halohydrocarbon mixture described above) | 89 |
| Vitavax (5,6-dihydro-2-methyl-1,4-oxathin-3-carboxanilide, also known as carboxin) | 118 |
| Azodrin (dimethyl phosphate of 3-hydroxy-N-methyl-cis-crotonamide, also known as monocrotophs) | 130 |
| Acetone | 106 |

This formulation was applied as a coating to seeds of cockleburs, cotton, soybeans and rice. After treatment of the seed some were planted immediately, some after storage in sealed metal containers for two weeks and some after three months. Table 2-A illustrates the results of seedling emergence.

Table 2-A

Seedling emergence (germination of cocklebur and cottonseed after coating or treatment with the above formulation). States periods of seed storage at room temperature in sealed metal containers.

| Kind of seed used | Rate Oz./Cwt. | Percent germination[1] following a storage period of: | | |
|---|---|---|---|---|
| | | None | 2 Weeks | 3 Months |
| Cottonseed | 0 | 82 | 80 | 82 |
| | 4 | 84 | 86 | 84 |
| | 8 | 86 | 84 | 82 |
| | 12 | 84 | 85 | 86 |
| | 24 | 84 | 84 | 84 |
| Cocklebur seed | 0 | 40 | 40 | 40 |
| | 4 | 30 | 20 | 0 |
| | 12 | 40 | 15 | 0 |
| | 48 | 30 | 10 | 0 |
| | 0 | 38 | 42 | 44 |

[1]=Seven days after planting.

As can be seen from the data, the effect on cocklebur seed is enhanced by storage in a sealed container. Preferably, the treated seed is stored for at least about one week. Alternatively, the seed can be treated with vapor phase $C_3$ halohydrocarbon for a time sufficient to obtain absorption of a germination retarding amount of the halohydrocarbon.

Additional cottonseed were also coated with the above formulation of Nemagon, carboxin, monocrotophos and acetone as described in Table 2. The seed was planted (after several storage periods) in fields near Shreveport, Louisiana, St. Joseph, Louisiana, Memphis, Tennessee, Vail, Arkansas and Midland, Texas. Percentage emergence after 14 days and average weights of 50 seedlings after 42 days were recorded. Included in the tests were an untreated check (1); a treated check (2) consisting of a wettable powder containing Captan 50%, Vitavax 75% and monocrotophos; the above formulation from sealed containers (3); and from unsealed containers (4). These results are reported in Table 2-B.

Table 2-B

Percentage field emergence of cottonseedlings after 14 days and average weight in grams of 50 seedlings after 42 days following stated seed treatments and storage conditions at stated locations.

| Seed treatments used | Vail, Ark. | Memphis, Tenn. | St. Joseph, La. | Shreveport, La. |
|---|---|---|---|---|
| | Percent emergence after 14 days | | | |
| Untreated Check[1] | 71 | 71 | | 66 |
| Stored, sealed 2 weeks[3] | 79 | 80 | | — |
| Stored not sealed 2 weeks[4] | 72 | 79 | | 83 |
| Slurry formulation[2] | 87 | 84 | 83 | |
| | Seedling wt. (gms.) after 42 days | | | |
| Untreated Check[1] | 163 | 156 | | 771 |
| Stored, sealed 2 weeks[3] | 220 | 176 | | — |
| Stored not sealed[4] | 226 | 178 | | 875 |
| Slurry formulation[2] | 191 | 222 | | 824 |

[1]=Untreated cottonseed.
[2]=A slurry formulation consisting of Captan 50%, 90 gms.; Vitavax 17%, 480 gms. and monocrotophos 100%, 146 gms. in 80 grams acetone and water, at rate of 32 oz./cwt. of seed.
[3]=Nemagon 89 gms., carboxin 118 gms., monocrotophos 130 gms. and acetone 106 gms. at the rate of 12 fl. oz./cwt. of seed stored in sealed containers 2 weeks.
[4]=Same formulation as 3 not stored in sealed container.

The tolerance of cotton and soybean seed to the above formulation of Nemagon, carboxin, monocrotophos and acetone, applied as a coating on the seed at various rates was determined by a field planting near Memphis, Tennessee. The results are shown in Table 2-C.

Table 2-C

Tolerance of cotton and soybean seed to the formulation of Nemagon, carboxin, monocrotophos and acetone in field soil near Memphis, Tenn., as measured by seedling survival after 30 days.

| Seed used | Seedling survival and seedling weight 30 days after planting | | | | | |
|---|---|---|---|---|---|---|
| | oz./cwt. | | | | | |
| | 0 | 3 | 6 | 12 | 24 | 48 |
| | Percent survival | | | | | |
| Cotton | 82 | 76 | 76 | 82 | 90 | 82 |
| Soybeans | 64 | 68 | 40 | 6 | 0 | 5 |
| | Weight of plants (gms.) | | | | | |
| Cotton | 130 | 110 | 108 | 135 | 170 | 128 |

EXAMPLE 3

A lot of acid delinted cottonseed (Var. DPL16) was divided into portions to which Nemagon C was applied using the following rates per 100 pounds of seeds: 3 oz., 6 oz., 12 oz., 24 oz., and 48 oz. 1% by weight of water was also added. An untreated control portion was also included. After treatment each lot was enclosed in a polyethylene bag. The wet seed were dry after approximately 24 hours, indicating the coating material was taken into the seed.

The seed were test planted in seed quality test kits (Ekol Corp.). There were no visible difference in emergence and growth of any of the seed lots during the 10 days test period, including the control seed.

The following table summarizes the results of the ten day test period.

Table 3

| Replicate No. | Emergence % | 1st Quality Seedlings % | 2nd Quality Seedlings % | Culls % | Diseased Seedlings % | Seedling Weight Gms. | Vigor Factor[a] |
|---|---|---|---|---|---|---|---|
| | | | 3 oz./100 lbs. | | | | |
| 1 | 82 | 74 | 6 | 2 | 0 | 32.8 | |
| 2 | 76 | 60 | 10 | 2 | 4 | 32.9 | |
| 3 | 68 | 54 | 12 | 2 | 0 | 29.8 | |
| Ave. | 75.3 | 62.7 | 9.3 | 2.0 | 1.3 | 31.8 | 6.3 |

Table 3-continued

| Replicate No. | Emergence % | 1st Quality Seedlings % | 2nd Quality Seedlings % | Culls % | Diseased Seedlings % | Seedling Weight Gms. | Vigor Factor[a] |
|---|---|---|---|---|---|---|---|
| | | | 6 oz./100 lbs. | | | | |
| 1 | 78 | 50 | 18 | 10 | 0 | 31.5 | |
| 2 | 82 | 56 | 22 | 2 | 2 | 38.6 | |
| 3 | 76 | 40 | 30 | 6 | 0 | 32.9 | |
| Ave. | 78.7 | 48.7 | 23.3 | 5.3 | 0.7 | 34.3 | 6.8 |
| | | | 12 oz./100 lbs. | | | | |
| 1 | 88 | 60 | 10 | 18 | 0 | 39.0 | |
| 2 | 82 | 52 | 24 | 6 | 0 | 39.8 | |
| 3 | 88 | 64 | 12 | 12 | 0 | 32.3 | |
| Ave. | 86 | 58.7 | 15.3 | 12 | 0 | 37.0 | 7.3 |
| | | | 24 oz./100 lbs. | | | | |
| 1 | 76 | 46 | 14 | 8 | 8 | 28.9 | |
| 2 | 90 | 64 | 22 | 4 | 0 | 39.6 | |
| 3 | 75 | 38 | 32 | 4 | 1 | 25.6 | |
| Ave. | 80.3 | 49.3 | 22.7 | 5.3 | 3 | 31.4 | 7.8 |
| | | | 48 oz./100 lbs. | | | | |
| 1 | 82 | 60 | 10 | 12 | 0 | 34.9 | |
| 2 | 78 | 62 | 14 | 2 | 0 | 32.7 | |
| 3 | 64 | 28 | 34 | 2 | 0 | 32.0 | |
| Ave. | 74.7 | 50 | 19.3 | 5.3 | 0 | 33.2 | 6.6 |
| Ave. Total | | | | | | | 7.0 |
| | | | Untreated Check | | | | |
| 1 | 72 | 48 | 15 | 8 | 0 | 32.0 | |
| 2 | 82 | 56 | 14 | 10 | 2 | 34.7 | |
| 3 | 83 | 57 | 20 | 6 | 0 | 33.4 | |
| Ave. | 79 | 53.7 | 16.7 | 8.0 | 0.7 | 33.4 | 6.7 |

[a]Average weight of individual seedling in grams (50 planted seed) × percent survival ÷ 10. The higher the number the better the seed quality. (See Pinckard & Melville, Plant Disease Reporter Vol. 59)

Where a mixture of cottonseed and cocklebur seed, treated as above, are planted, the germination of the cocklebur seed is significantly retarded.

A blend or formulation comprising a solution containing the $C_3$ halohydrocarbon, carboxin and/or monocrotophos, including those described above, has substantial commercial value for the sole reason that, even disregarding any activity of the $C_3$ halohydrocarbon, the halohydrocarbon provides a solution with carboxin, monocrotophos, Demosan or other agricultural adjuvants, e.g., pesticides, particularly fungicides and insecticides, particularly systemic pesticides, which has a lower freezeout point than present commercial formulation. The use of the halohydrocarbons as at least a portion of the solvent allows the preparation of active materials which can be handled as liquids with less attention to preventing freezeout. Monocrotophos will crystallize in its containers at temperatures below 60° F. and carboxin has heretofore been formulated commercially only as a 75% wettable powder because of its insolubility in common solvents. It therefore now requires formulation as a slurry for seed treatment applications. As a result of this invention carboxin may now be applied as a solution. Nemagon freezes at 40° F. The solutions formed containing inter alia the halohydrocarbon, carboxin and monocrotophos remain liquid at 36° F. and precipitate as fine crystals at lower temperatures, returning to a true solution when merely warmed or subjected to moderate agitation to speed the process.

A similar formulation using Demosan (a product competitive with Vitavax) may be made by using the halohydrocarbons as the solvent.

The amount of halohydrocarbon in the solution is not critical so long as a solution is formed. Preferably, the amount of the halohydrocarbon is that amount described as effective above. The preferred solvent blends comprise a mixture of the halohydrocarbon and aceton or a mixture of the halohydrocarbon, acetone and water.

According to the provisions of the Patent Statutes, there are described above the invention and what are now considered its best embodiments; however, within the scope of the appended claims, it is to be understood that the invention can be practiced otherwise than as specifically described.

What is claimed is:

1. A mixture of cottonseed and cocklebur seed having seeds coated and surface penetrated with a cocklebur seed germination reducing amount, between about 0.1 to about 5% by weight based on the total weight of the seed mixture, of at least one $C_3$ saturated or ethylinically unsaturated halohydrocarbon where the halogen is chlorine or bromine or mixtures thereof.

2. A seed mixture, as in claim 1 where about 0.1 to about 3% of the halohydrocarbon is employed.

3. A seed mixture, as in claim 2, where about 0.2 to about 0.5% of the halohydrocarbon is employed.

4. A seed mixture, as in claim 1, where the halogen is chlorine or mixtures of chlorine and bromine.

5. A seed mixture, as in claim 1, where the halohydrocarbon is selected from the group consisting of 1,3-dichloropropene, 3,3-dichloropropene, 1,2-dichloropropane, 2,3-dichloropropene, and 1,2-dibromo-3-chloropropane or mixtures thereof.

6. A seed mixture, as in claim 5, where about 0.1 to about 3% of the halohydrocarbon is employed.

7. A seed mixture, as in claim 6, where about 0.2 to about 0.5% of the halohydrocarbon is employed.

8. A seed mixture, as in claim 1, wherein the halohydrocarbon is a mixture of $C_3$ chlorinated hydrocarbons containing a minimum of 50 weight percent of 1,3-dichloropropene-1.

9. A seed mixture, as in claim 1, wherein the halohydrocarbon is 1,2-dibromo-3-chloropropane.

10. A method for reducing the germination of cocklebur seed in a mixture of cottonseed and cocklebur seed at least without harm to the cottonseed which comprises contacting and penetrating the seed surface of the seeds in said seed mixture with at least one $C_3$ saturated or ethylinically unsaturated halohydrocarbon where the halogen is chlorine or bromine or mixtures thereof, in a cocklebur seed germination reducing amount, between about 0.1 to about 5% by weight based on the total weight of the seed mixture.

11. The method, as in claim 10, where the halohydrocarbon is selected from the group consisting of 1,3-dichloropropene, 3,3-dichloropropene, 1,2-dichloropropane, 2,3-dichloropropene, and 1,2-dibromo-3-chloropropane or mixtures thereof.

12. The method, as in claim 11, where about 0.1 to about 3% of the halohydrocarbon is employed.

13. The method, as in claim 12, where about 0.2 to about 0.5% of the halohydrocarbon is employed.

14. The method, as in claim 11, wherein the halohydrocarbon is a mixture of $C_3$ chlorinated hydrocarbons containing a minimum of 50 weight percent of 1,3-dichloropropene-1.

15. The method, as in claim 11, wherein the halohydrocarbon is 1,2-dibromo-3-chloropropane.

* * * * *